(12) United States Patent
Vitello

(10) Patent No.: US 10,166,347 B1
(45) Date of Patent: Jan. 1, 2019

(54) CLOSURE ASSEMBLY FOR A MEDICAL DEVICE

(71) Applicant: Patrick Vitello, Fort Lauderdale, FL (US)

(72) Inventor: Patrick Vitello, Fort Lauderdale, FL (US)

( * ) Notice: Subject to any disclaimer, the term of this patent is extended or adjusted under 35 U.S.C. 154(b) by 515 days.

(21) Appl. No.: 14/804,025

(22) Filed: Jul. 20, 2015

Related U.S. Application Data

(60) Provisional application No. 62/026,205, filed on Jul. 18, 2014.

(51) Int. Cl.
*A61M 5/50* (2006.01)

(52) U.S. Cl.
CPC ................ *A61M 5/5086* (2013.01)

(58) Field of Classification Search
CPC ............. A61M 5/5086; A61M 5/3134; A61M 2005/3104; A61M 2205/583; A61M 5/28; A61M 2005/312; A61M 2039/1033; A61M 2039/1083; A61M 2205/60; A61M 2205/6063; A61M 39/10; A61M 39/1011; A61M 5/3202; A61M 39/20; A61M 2205/273; A61M 5/3213
See application file for complete search history.

(56) References Cited

U.S. PATENT DOCUMENTS

| | | | |
|---|---|---|---|
| 732,662 A | 6/1903 | Smith | |
| 1,678,991 A | 7/1928 | Marschalek | |
| 1,970,631 A | 8/1934 | Sherman | |
| 2,477,598 A | 2/1948 | Hain | |
| 2,739,590 A | 3/1956 | Yochem | |
| 2,823,674 A | 2/1958 | Yochem | |
| 2,834,346 A | 5/1958 | Adams | |
| 2,875,761 A | 3/1959 | Helmer et al. | |
| 2,888,015 A | 5/1959 | Hunt | |
| 2,952,255 A | 9/1960 | Hein, Jr. | |
| 3,122,280 A | 2/1964 | Goda | |
| 3,245,567 A | 4/1966 | Knight | |
| 3,323,798 A | 6/1967 | Miller | |
| 3,364,890 A | 1/1968 | Andersen | |
| 3,412,749 A | 11/1968 | McAdams et al. | |
| 3,598,120 A | 8/1971 | Mass | |
| 3,610,241 A | 10/1971 | LeMarie | |
| 3,700,215 A | 10/1972 | Hardman et al. | |
| 3,706,307 A | 12/1972 | Hasson | |
| 3,747,751 A | 4/1973 | Miller et al. | |
| 3,872,867 A | 3/1975 | Killinger | |

(Continued)

FOREIGN PATENT DOCUMENTS

| | | |
|---|---|---|
| EP | 0148116 | 7/1985 |
| WO | WO 2017/086607 | 5/2017 |

*Primary Examiner* — Brandy S Lee
(74) *Attorney, Agent, or Firm* — Malloy & Malloy, P.L.

(57) ABSTRACT

A closure assembly for a medical device structured to provide an indication of tampering comprising an outer sleeve including an indicator window formed therein. An end cap is connected to the sleeve and movable there with and includes an indicator shield attached thereto. A tip cap is movably retained within the sleeve and includes an indicator member movable with the tip cap and detachable therefrom. The indicator window is disposed in visual alignment with either the indicator member or the indicator shield dependent on a state of use of the closure assembly.

6 Claims, 8 Drawing Sheets

(56) References Cited

U.S. PATENT DOCUMENTS

| | | | |
|---|---|---|---|
| 3,905,375 | A | 9/1975 | Toyama |
| 3,937,211 | A | 2/1976 | Merten |
| 4,043,334 | A | 8/1977 | Brown et al. |
| 4,046,145 | A | 9/1977 | Choksi et al. |
| 4,216,585 | A | 8/1980 | Hatter |
| 4,216,872 | A | 8/1980 | Bean |
| 4,244,366 | A | 1/1981 | Raines |
| 4,252,122 | A | 2/1981 | Halvorsen |
| 4,286,591 | A | 9/1981 | Raines |
| 4,313,539 | A | 2/1982 | Raines |
| 4,420,085 | A | 12/1983 | Wilson et al. |
| 4,430,077 | A | 2/1984 | Mittleman et al. |
| 4,457,445 | A | 7/1984 | Hanks et al. |
| 4,521,237 | A | 6/1985 | Logothetis |
| 4,530,697 | A | 7/1985 | Kuhlemann et al. |
| 4,571,242 | A | 2/1986 | Klein et al. |
| 4,589,171 | A | 5/1986 | McGill |
| 4,667,837 | A | 5/1987 | Vitello et al. |
| 4,693,707 | A | 9/1987 | Dye |
| 4,726,483 | A | 2/1988 | Drozd |
| 4,743,229 | A | 5/1988 | Chu |
| 4,743,231 | A | 5/1988 | Kay et al. |
| 4,760,847 | A | 8/1988 | Vaillancourt |
| 4,832,695 | A | 5/1989 | Rosenberg et al. |
| 4,834,706 | A | 5/1989 | Beck et al. |
| 4,842,592 | A | 6/1989 | Caggiani et al. |
| 4,844,906 | A | 7/1989 | Hermelin et al. |
| 4,906,231 | A | 3/1990 | Young |
| 4,919,285 | A | 4/1990 | Roof et al. |
| 5,009,323 | A | 4/1991 | Montgomery et al. |
| 5,049,129 | A | 9/1991 | Zdeb et al. |
| 5,051,093 | A | 10/1991 | Clegg et al. |
| 5,135,496 | A | 8/1992 | Vetter et al. |
| 5,165,560 | A | 11/1992 | Ennis, III et al. |
| 5,230,429 | A | 7/1993 | Etheredge, III |
| 5,267,983 | A | 12/1993 | Oilschlager et al. |
| 5,292,308 | A | 3/1994 | Ryan |
| 5,295,599 | A | 3/1994 | Smith |
| 5,328,466 | A | 7/1994 | Denmark |
| 5,328,474 | A | 7/1994 | Raines |
| 5,356,380 | A | 10/1994 | Hoekwater et al. |
| 5,380,295 | A | 1/1995 | Vacca |
| 5,405,339 | A | 4/1995 | Kohnen et al. |
| 5,458,580 | A | 10/1995 | Hajishoreh |
| 5,468,224 | A | 11/1995 | Souryal |
| 5,531,695 | A | 7/1996 | Swisher |
| 5,540,666 | A | 7/1996 | Barta et al. |
| 5,549,571 | A | 8/1996 | Sak |
| 5,558,648 | A | 9/1996 | Shields |
| 5,584,817 | A | 12/1996 | van den Haak |
| 5,624,402 | A | 4/1997 | Imbert |
| 5,674,209 | A | 10/1997 | Yarger |
| 5,700,247 | A | 12/1997 | Grimard et al. |
| 5,702,374 | A | 12/1997 | Johnson |
| 5,776,124 | A | 7/1998 | Wald |
| 5,785,691 | A | 7/1998 | Vetter et al. |
| 5,797,885 | A | 8/1998 | Rubin |
| 5,807,343 | A | 9/1998 | Tucker et al. |
| 5,883,806 | A | 3/1999 | Meador et al. |
| 5,884,457 | A | 3/1999 | Ortiz et al. |
| 5,902,269 | A | 5/1999 | Jentzen |
| 5,951,522 | A | 9/1999 | Rosato et al. |
| 5,951,525 | A | 9/1999 | Thorne et al. |
| 5,954,657 | A | 9/1999 | Rados |
| 5,957,166 | A | 9/1999 | Safabash |
| 5,989,227 | A | 11/1999 | Vetter et al. |
| 6,000,548 | A | 12/1999 | Tsals |
| 6,021,824 | A | 2/2000 | Larsen et al. |
| 6,027,482 | A | 2/2000 | Imbert |
| 6,068,614 | A | 5/2000 | Kimber et al. |
| 6,126,640 | A | 10/2000 | Tucker et al. |
| 6,190,364 | B1 | 2/2001 | Imbert |
| 6,193,688 | B1 | 2/2001 | Balestracci et al. |
| 6,196,998 | B1 | 3/2001 | Jansen et al. |
| 6,280,418 | B1 | 8/2001 | Reinhard et al. |
| 6,322,543 | B1 | 11/2001 | Singh et al. |
| 6,338,200 | B1 | 1/2002 | Baxa et al. |
| 6,375,640 | B1 | 4/2002 | Teraoka |
| 6,394,983 | B1 | 5/2002 | Mayoral et al. |
| 6,485,460 | B2 | 11/2002 | Eakins et al. |
| 6,500,155 | B2 | 12/2002 | Sasso |
| 6,520,935 | B1 | 2/2003 | Jansen et al. |
| 6,540,697 | B2 | 4/2003 | Chen |
| 6,565,529 | B1 | 5/2003 | Kimber et al. |
| 6,581,792 | B1 | 6/2003 | Limanjaya |
| 6,585,691 | B1 * | 7/2003 | Vitello ................ A61M 5/3134 215/230 |
| 6,592,251 | B2 | 7/2003 | Edwards et al. |
| 6,726,652 | B2 | 4/2004 | Eakins et al. |
| 6,726,672 | B1 | 4/2004 | Hanley et al. |
| 6,775,220 | B2 | 6/2004 | Castellano et al. |
| 6,764,469 | B2 | 7/2004 | Broselow |
| 6,821,268 | B2 | 11/2004 | Balestracci |
| 6,921,383 | B2 | 7/2005 | Vitello |
| 6,942,643 | B2 | 9/2005 | Eakins et al. |
| 7,141,286 | B2 | 11/2006 | Kessler et al. |
| 7,182,256 | B2 | 2/2007 | Andreasson et al. |
| 7,240,926 | B2 | 7/2007 | Dalle et al. |
| 7,374,555 | B2 | 5/2008 | Heinz et al. |
| 7,404,500 | B2 | 7/2008 | Marteau et al. |
| 7,410,803 | B2 | 8/2008 | Nollert et al. |
| 7,425,208 | B1 | 9/2008 | Vitello |
| 7,437,972 | B2 | 10/2008 | Yeager |
| 7,482,166 | B2 | 1/2009 | Nollert et al. |
| 7,588,563 | B2 | 9/2009 | Guala |
| 7,594,681 | B2 | 9/2009 | DeCarlo |
| 7,632,244 | B2 | 12/2009 | Buehler et al. |
| 7,641,636 | B2 | 1/2010 | Moesli et al. |
| 7,735,664 | B1 | 6/2010 | Peters et al. |
| 7,748,892 | B2 | 7/2010 | McCoy |
| 7,762,988 | B1 | 7/2010 | Vitello |
| 7,766,919 | B2 | 8/2010 | Delmontte |
| 7,802,313 | B2 | 9/2010 | Czajka |
| 7,918,830 | B2 | 4/2011 | Langan et al. |
| 8,079,518 | B2 | 12/2011 | Turner et al. |
| 8,091,727 | B2 | 1/2012 | Domkowski |
| 8,137,324 | B2 | 3/2012 | Bobst |
| 8,140,349 | B2 | 3/2012 | Hanson et al. |
| 8,257,286 | B2 | 9/2012 | Meyer et al. |
| 8,328,082 | B1 | 12/2012 | Bochenko et al. |
| 8,348,895 | B1 | 1/2013 | Vitello |
| 8,353,869 | B2 | 1/2013 | Ranalletta et al. |
| 8,443,999 | B1 | 5/2013 | Reinders |
| D684,057 | S | 6/2013 | Kwon |
| 8,512,277 | B2 | 8/2013 | Del Vecchio |
| 8,556,074 | B2 | 10/2013 | Turner et al. |
| 8,579,116 | B2 | 11/2013 | Pether et al. |
| 8,591,462 | B1 | 11/2013 | Vitello |
| 8,597,255 | B2 | 12/2013 | Emmott et al. |
| 8,597,271 | B2 | 12/2013 | Langan et al. |
| 8,616,413 | B2 | 12/2013 | Koyama |
| D701,304 | S | 3/2014 | Lair et al. |
| 8,672,902 | B2 | 3/2014 | Ruan et al. |
| 8,702,674 | B2 | 4/2014 | Bochenko |
| 8,777,930 | B2 | 7/2014 | Swisher et al. |
| 8,852,561 | B2 | 10/2014 | Wagner et al. |
| 8,864,021 | B1 | 10/2014 | Vitello |
| 8,864,707 | B1 | 10/2014 | Vitello |
| 8,864,708 | B1 | 10/2014 | Vitello |
| 8,945,082 | B2 | 2/2015 | Geiger et al. |
| 9,101,534 | B2 | 8/2015 | Bochenko |
| 9,199,042 | B2 | 12/2015 | Farrar et al. |
| 9,199,749 | B1 | 12/2015 | Vitello |
| 9,220,486 | B2 | 12/2015 | Schweiss et al. |
| 9,220,577 | B2 | 12/2015 | Jessop et al. |
| 9,272,099 | B2 | 3/2016 | Limaye et al. |
| 9,311,592 | B1 | 4/2016 | Vitello |
| D756,777 | S | 5/2016 | Berge et al. |
| 9,336,669 | B2 | 5/2016 | Bowden et al. |
| D759,486 | S | 6/2016 | Ingram et al. |
| 9,402,967 | B1 | 8/2016 | Vitello |
| 9,427,715 | B2 | 8/2016 | Palazzolo et al. |
| 9,433,768 | B2 | 9/2016 | Tekeste et al. |
| 9,463,310 | B1 | 10/2016 | Vitello |

(56) References Cited

U.S. PATENT DOCUMENTS

| | | |
|---|---|---|
| D773,043 S | 11/2016 | Insgram et al. |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,855,191 B1 | 1/2018 | Vitello |
| D815,945 S | 4/2018 | Fischer et al. |
| D825,746 S | 8/2018 | Davis et al. |
| 2002/0023409 A1 | 2/2002 | Py |
| 2002/0133119 A1 | 9/2002 | Eakins et al. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2008/0068178 A1 | 3/2008 | Meyer |
| 2008/0097310 A1 | 4/2008 | Buehler et al. |
| 2009/0099552 A1 | 4/2009 | Levy et al. |
| 2009/0149815 A1 | 6/2009 | Kiel et al. |
| 2009/0158110 A1 | 6/2009 | Park et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1* | 2/2011 | Schiller .............. A61M 5/28 604/111 |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2014/0135738 A1 | 5/2014 | Panian |
| 2014/0155868 A1 | 6/2014 | Nelson et al. |
| 2015/0305982 A1 | 10/2015 | Bochenko |
| 2016/0067422 A1 | 3/2016 | Davis et al. |
| 2016/0144119 A1 | 5/2016 | Limaye et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0014310 A1 | 1/2017 | Hyun et al. |
| 2017/0173321 A1 | 6/2017 | Davis et al. |
| 2017/0203086 A1 | 7/2017 | Davis |
| 2017/0319438 A1 | 11/2017 | Davis et al. |

* cited by examiner

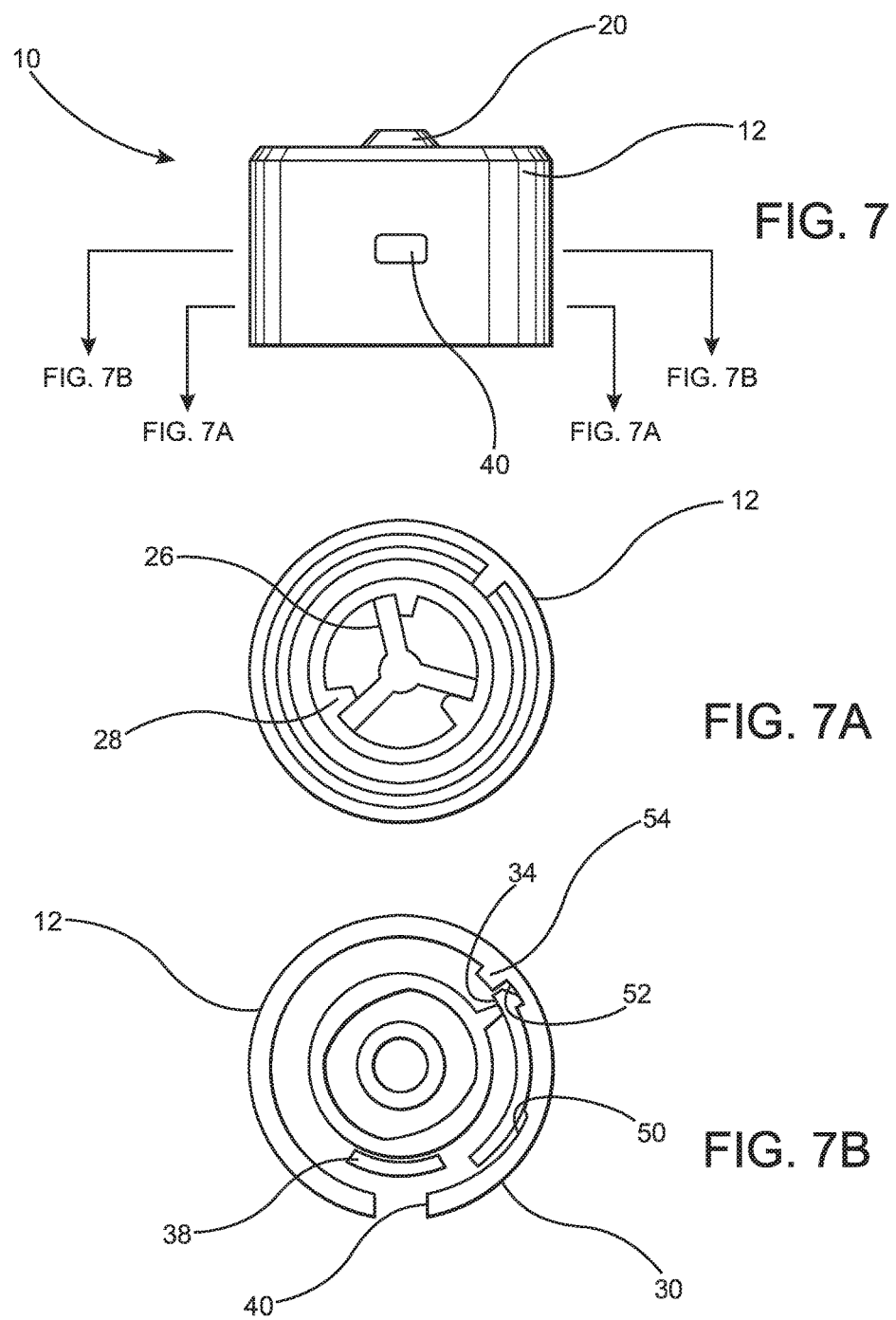

CLOSURE ASSEMBLY FOR A MEDICAL DEVICE

CLAIM OF PRIORITY

The present Non-Provisional patent application claims priority pursuant to 35 U.S.C. Section 119(e) to a prior filed Provisional patent application, namely, that having Ser. No. 62/026,205 filed on Jul. 18, 2014, the contents of which are incorporated herein by reference in its entirety.

BACKGROUND OF THE INVENTION

Field of the Invention

This invention is directed to a tamper evident closure assembly for use with a fitting for a medical device including, but not limited to, a female fitting and/or an enteral female fitting. The closure assembly includes a flow restrictive cap having an indicator member removably connected thereto and initially disposed within an outer sleeve or other housing having a window formed therein. Rotation of the closure assembly, once connected to the medical fitting, with sufficient force results in the indicator member becoming detached, and yet captured within the housing. The closure assembly includes components made of at least two different colors, so that a color viewable through the window will serve as a visual aid in determining if the closure assembly has been tampered with and/or used.

Description of the Related Art

In hospitals or other medical care facilities, it is very common for medical doctors and other authorized medical personnel to order that a patient be given a drug or medication by injection. In fact, it is currently estimated that more than 16 billion injections are administered on a worldwide basis in any given year.

As a result, it is becoming relatively common in hospital settings for a number of syringes to be pre-loaded or filled by a pharmacist, or other authorized personnel within a hospital or similar facility, at an appropriate location for subsequent dispensing to one or more patients. The pharmacy or other location where syringes are filled can and often will be located in a remote part of the hospital, relative to the patient care area where the injection is to be administered. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations are typically remotely located from a syringe filling station, a loaded syringe is quite often given to another person for delivery to a nurse's station, for subsequent dosing of the patient by qualified personnel. From the foregoing, it may be understood that during the course of loading a syringe with a drug, and delivering the loaded syringe to a nurse's station or to a patient, the syringe can easily be handled by numerous personnel.

Also, and especially in the case of a very expensive drug or an addictive drug, there is some danger that a pre-loaded syringe will be tampered with by a person seeking to improperly gain access to the drug. A resulting danger also exists relating to the possibility of inappropriately substituting saline solution or some other unauthorized substance for the intended medication originally loaded into the syringe. Thus, the growing use of syringes which are pre-loaded with a drug presents another problem in that it is important to know if the pre-loaded syringe has, or has not, been tampered with, exposed to contamination or otherwise compromised.

The benefits of using a pre-filled syringe and the ability to readily determine whether or not it has been tampered with, are abundantly clear. At the same time, however, drugs and medications are specific to each particular patient's disorder or disease being treated, and in addition, interactions between drugs and medications given to a patient incorrectly can have serious and deadly consequences. It is, therefore, important to know that a particular medication being injected is, in fact, the drug that was prescribed by the treating physician, and that it has not been replaced by another compound. Moreover, some drugs can have harmful effects in large doses. Accordingly, it is also important to ensure that the proper dosage is followed, as prescribed. Since pre-filled syringes are prepared in advance of being delivered and used, they may be loaded carefully by a pharmacist or other similarly qualified individual to ensure the appropriate medication and dose is prepared. This reduces errors on injection by nurses or physicians who may be in a stressful or time-sensitive situation and may not have the luxury of verifying the correct medication or measuring out a dose, particularly small doses, from a source vial.

There has historically been a problem, however, of knowing if a sealed, preloaded syringe has, or has not, been compromised by it being tampered with or if it might otherwise have a loss of sterility or have become contaminated. This and related types of problems have been described in the inventor's own previously granted U.S. Pat. No. 4,667,837 and in other patents, such as U.S. Pat. No. 5,328,474. Despite attempts in the past to prevent unauthorized access to syringe(s) pre-loaded with a drug or medication, it is understood that some problems continue to exist in this field of art and there remains an ongoing need for further improvements, despite the introduction of inventive products according to the above-noted two patents and others.

For instance, there remain problems of manufacturing such products in a manner which is relatively easy and inexpensive, as well as some problems involved with the assembly and placement onto a drug loaded syringe, such as at a drug filling station. Other problems exist relative to maintaining the sterility during storage at the manufacturing facility of some caps for syringes, and during transport of them to a hospital or other medical facility, during storage of them at a hospital or other medical facility, including any transport to a nursing station and ultimately, to a patient care area.

Accordingly, there is a need in this area for an improved closure assembly having the structural versatility to be used as a closure cap or closure cap or syringe cap or as a tamper evident cap (TEC), wherein the proposed closure assembly can be used in either capacity with standard or conventional pre-loaded syringe in a manner which overcomes problems and or disadvantages of the type set forth above. The development of any such improved closure assembly would preferably offer certain features such as, but not limited to, the cooperative structuring of a connecting structure which enables the proposed closure assembly to be connected to and removed from the nozzle or access portion of a pre-loaded syringe by a "push-on" connection and a "rotate-off" disconnection. In addition, if any such improved, closure assembly were developed, it would ideally be structurally and operatively reliable, while still remaining relative easy and cost effective to make and assemble, in order to facilitate widespread use and acceptance through-out the medical profession.

From the foregoing, one might appreciate that the present invention seeks to address such problems and others associated with closure assemblies for preloaded syringes including, but not limited to, tamper evident caps and luer lock caps during their manufacture, assembly and/or use.

SUMMARY OF THE INVENTION

The present invention relates to a closure assembly for a medical device that is structured and well suited to provide an indication as to whether it has been tampered with to access the drug or contents of the medical device to which it is connected. As illustrated and further described herein, the closure assembly comprises in one embodiment, a first component in the form of an outer sleeve including an indicator window, and a second component in the form of an end cap connected to the sleeve and movable therewith, and with the end cap further including an indicator shield. In addition, the closure assembly comprises another component in the form of a tip cap that is movably retained within the outer sleeve and includes an indicator member movable with said tip cap and detachable therefrom, and further, wherein the indicator window associated with the outer sleeve is disposed in visual alignment with either the indicator member of the tip cap or the indicator shield of the end cap, dependent upon whether the closure assembly, once assembled and installed on a medical device, is in an original state of not being used, or alternatively, after the closure assembly has been tampered with or used.

It is also an object of the present invention to provide a closure assembly that provides evidence of use entirely, or almost entirely, through a color change appearing in the window of the outer sleeve.

It is also an object of the present invention to provide a closure assembly that provides such visible, color evidence of its having been used or tampered with, regardless of whether the assembly is installed on a fitting that is facing downwards or upwards, and so that gravity is not required to signal such evidence of use or tampering.

It is also an object of the present invention to provide a closure assembly that can be installed via rotation of the outer sleeve and that can be removed via rotation as well.

Yet another object of the present invention to provide a closure assembly that will ideally keep all of its components inside the assembly at all times, including after the assembly has been removed from the fitting.

A further object of the present invention is to effectively lock the indicator(s) as to the closure assembly having been used or tampered with in place after the removal of the closure assembly from a medical fitting.

BRIEF DESCRIPTION OF THE DRAWINGS

For a fuller understanding of the nature of the present invention, reference should be had to the following detailed description taken in connection with the accompanying drawings in which:

FIG. 7 is also an exterior view of the closure assembly illustrated in FIG. 1 in an assembled orientation, and is labeled as "State 3."

FIG. 7A is a sectional view of the interior of the closure assembly illustrated in FIG. 7, taken along lines B1-B1 of FIG. 7.

FIG. 7B is also sectional view of the interior of the closure assembly illustrated in FIG. 7, but taken along lines C1-C1 of FIG. 7.

Like reference numerals refer to like parts throughout the several views of the drawings.

DETAILED DESCRIPTION OF THE INVENTION IN A PREFERRED EMBODIMENT

Figure 1:
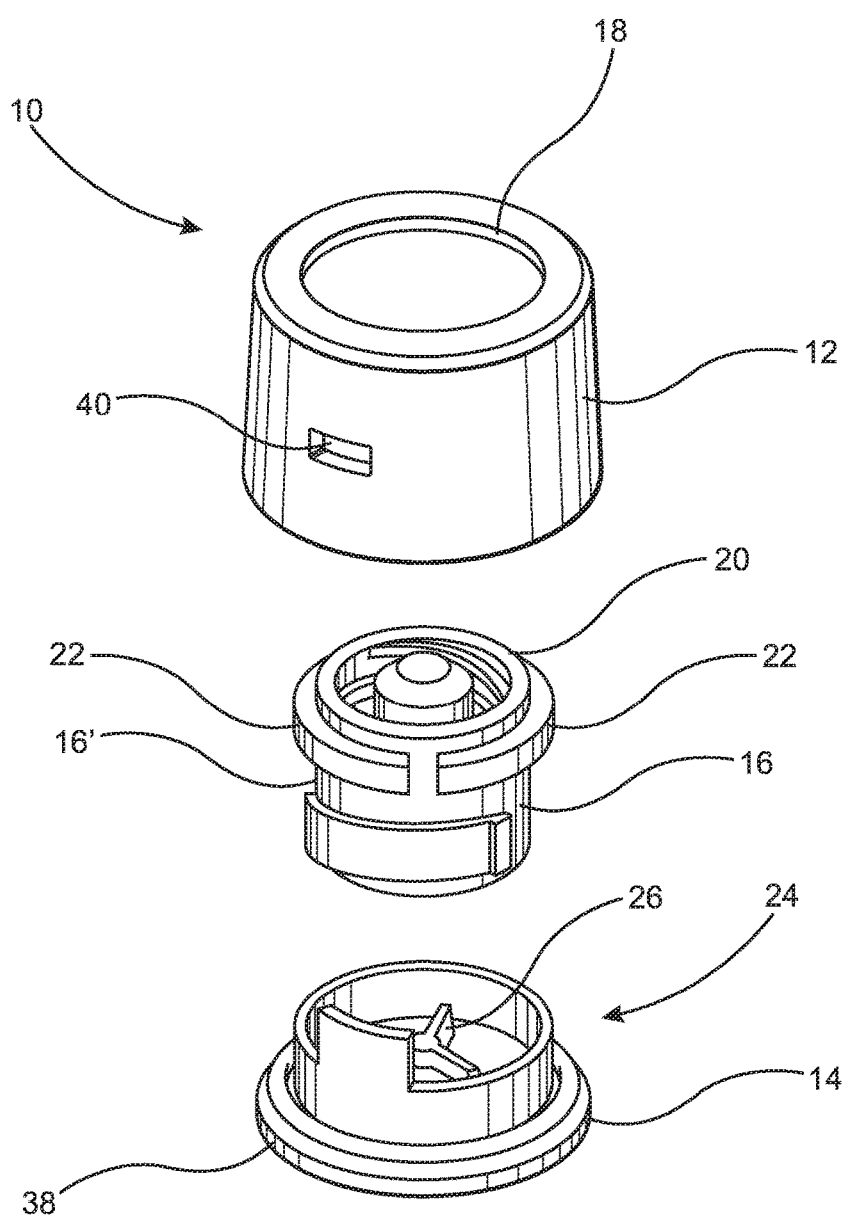
FIG. 1 is a perspective view in exploded form of a closure assembly in accordance with the present invention.

As represented in the accompanying Figures and with initial reference to FIG. 1, the present invention is directed to a closure assembly, generally indicated as 10, for an enteral fitting and/or a number of medical devices such as, but not limited to, a needleless syringe. When so attached, in an intended operative position, the closure assembly 10 provides a sealing engagement with a cooperatively structured enteral component/fitting or other medical device, as indicated.

Figure 2:
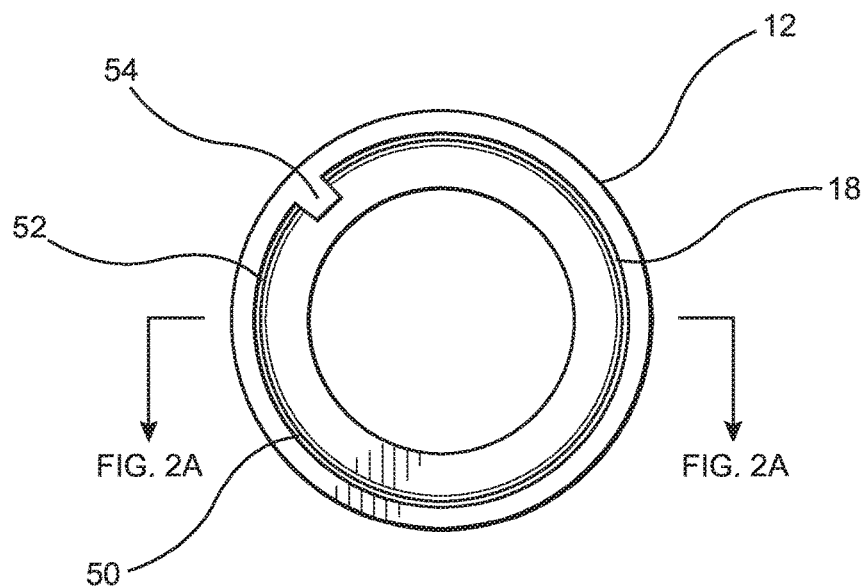
FIG. 2 is a bottom interior view of a first component associated with the closure assembly illustrated in FIG. 1.
Figure 2A:
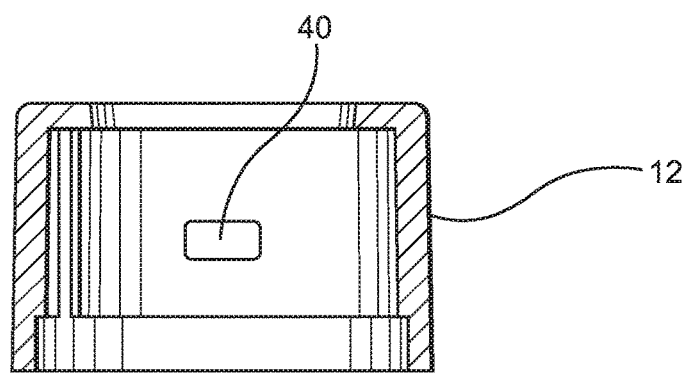
FIG. 2A is a sectional, interior view of the component shown in FIG. 2, taken along the lines A-A thereof.
Figure 3:
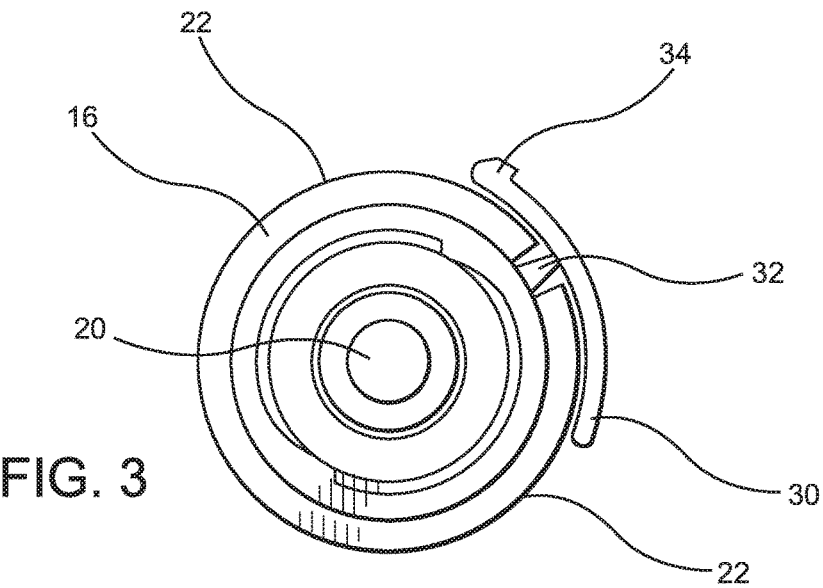
FIG. 3 is a plan view of another component associated with the closure assembly illustrated in FIG. 1.
Figure 3A:
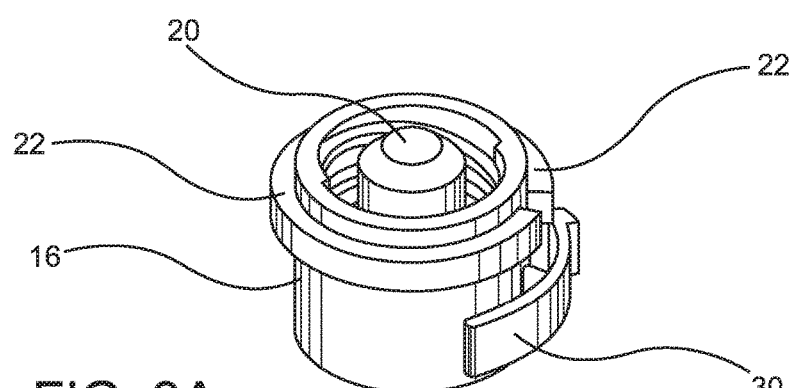
FIG. 3A is a perspective view of the component illustrated in FIG. 3 and illustrating a partial view from the top of the interior thereof.
Figure 3B:
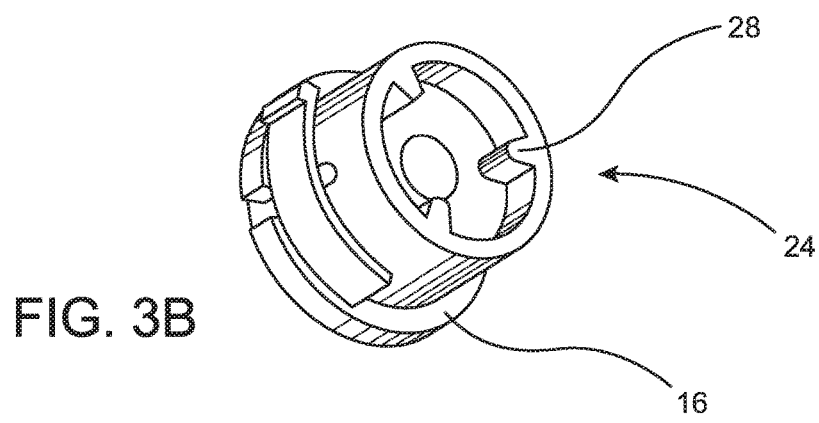
FIG. 3B is also a perspective view of the component illustrated in FIGS. 3 and 3A, but illustrates a bottom of the interior thereof.
Figure 4:
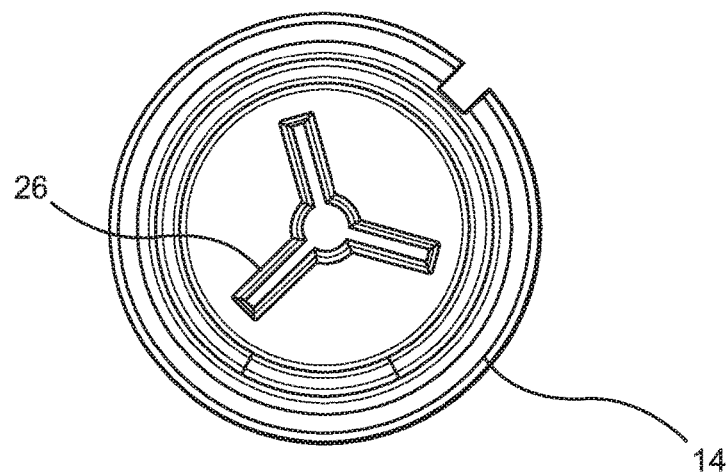
FIG. 4 is an interior view of yet another component associated with the closure assembly illustrated in FIG. 1.
Figure 4A:
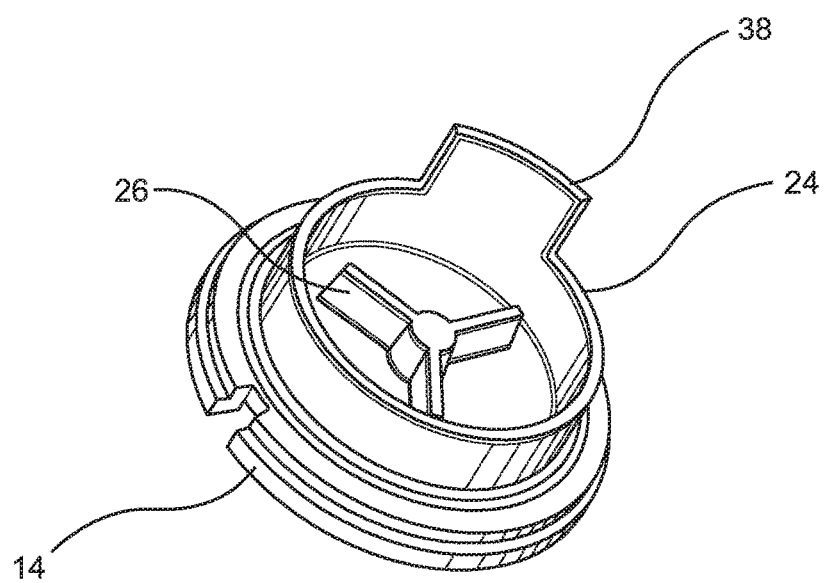
FIG. 4A is a perspective view of the component illustrated in FIG. 4 and illustrating a partial interior view thereof.

More specifically, the closure assembly 10 comprises a first component which is best illustrated in FIGS. 1, 2 and 2A, that includes an exterior sleeve 12 fixedly connected to and movable with another component, namely, an end cap 14 as is best illustrated in FIGS. 4 and 4A. In addition, the closure assembly comprises another component, namely, a tip cap 16 as is best illustrated in FIGS. 3, 3A and 3B. The tip cap 16 is retained within the interior of the sleeve 12 and is positioned for sealing engagement or other appropriate engagement with the cooperative structure associated with the enteral fitting or other medical device. Moreover, and as shown in FIG. 2 the sleeve 12 includes a central aperture 18, which provides access to the sealing plug 20 or a like sealing structure, that may include additional interior sections or components located within or associated with the tip cap 16. Still referring to FIGS. 3 through 3B, additional features of the tip cap 16 associated with the closure assembly 10 preferably include one or more guard members, comprising in a preferred embodiment, one or more guard rings 22 disposed about an outer periphery of the tip cap 16, as represented throughout the Figures. The one or more guard rings 22 are disposed and dimensioned to prevent passage of the tip cap 16 through the aperture 18 of the exterior sleeve 12. Therefore, the outer dimension of the one or more guard rings 22 is sized and structured to be larger or greater than the interior dimension of the aperture 18.

In addition, and with reference now to FIGS. 3, 3A and 3B as well as FIGS. 4 and 4A, in the illustrated embodiment both the tip cap 16 and the end cap 14 are cooperatively structured to include a primary drive mechanism, as generally indicated as 24. More specifically, the drive mechanism 24 includes a "spider" like finger structure or hub 26 secured to an interior surface 29 that is preferably located on the bottom of end cap 14. Due to this construction, rotation of the sleeve 12 and the fixedly attached end cap 14 will serve to rotate the drive member 26 in either of two opposite directions, such as in a clockwise ("CW") direction or in a counterclockwise ("CCW") direction. In cooperation therewith, the primary drive mechanism 24 further includes a plurality of spaced apart members 28 formed on the tip cap 16, which are structured and disposed to engage and/or be driven by the spider like finger structure or hub 26 defining the drive member 24 on the end cap 14, such as when the sleeve 12 and end cap 14 are rotated. Accordingly, and as explained in greater detail hereinafter, the tip cap 16 may be movable either selectively or "freely" within the interior of the sleeve 12 to facilitate attachment and removal of the tip cap 16 to the other, enteral structure on the medical device, as set forth above.

Yet additional structural and operative features associated with the closure assembly 10 are cooperatively disposed so as to provide at least a visual indication of either tampering and/or use of the closure assembly 10, at least in terms of being attached to and removed from a cooperative enteral component/fitting, or the like. More specifically, and as illustrated in FIGS. 3 and 3A, the tip cap 16 includes an indicator member 30 connected to an exterior of the tip cap 16 by means of a frangible tab 32. Further, the indicator member 30 preferably has a substantially elongated configuration with a protrusion 34 at one end thereof, as clearly represented in at least FIG. 3, to allow this component of the closure assembly 10 to offer a "snap feature." It is noted that the indicator member 30 extends sufficiently outward from the corresponding exterior surface 16' of the tip cap 16 so as to be initially disposed and moved within the interior of the sleeve 12 shown in FIG. 1, with the sleeve 12 in overlying relation thereto.

As also represented throughout the Figures, but perhaps best shown in FIG. 2A, the sleeve 12 includes a window 40 which allows at least some viewing and/or visual observation into the interior of the sleeve 12. More specifically, the window 40 is disposed in aligned relation to both the indicator member 30 associated with the tip cap 16 and to a shield 38, also referred to as an indicator shield herein, associated with the end cap 14. As the tip cap 16 is movable selectively within the interior of the sleeve 12, either the exterior of the indicator member 30 or the exterior surface of the shield 38 will be viewable through the window 40, dependent upon the relative position of the tip cap 16 to the end cap 14 and indicator shield 38 within the interior of the sleeve 12. This visual indication will provide what can be referred to as a "state of use" of the closure assembly 10, at least in terms of it being used and/or possibly tampered with.

It should be further noted that the color of the indicator member 30 associated with tip cap 16 is intended to be visually distinguishable from the color of the shield 38 associated with the end cap 14. By way of example only, and as explained in greater detail hereinafter, the color of the indicator member 30 could be green, while the color of the shield 38 could be red. This would provide a clear visual indication, through window 40 of sleeve 12, as to whether the closure assembly 10 is in an initial, unused and/or un-tampered state, such as when the "green" indicator member 30 is viewable through the window 40. In the alternative, if the closure assembly 10 has been already used or even if it has possibly been tampered with, that state of the closure assembly 10 would be visually indicated when the "red" shield 38 is viewable through the window 40, as explained in greater detail hereinafter.

Figure 5:
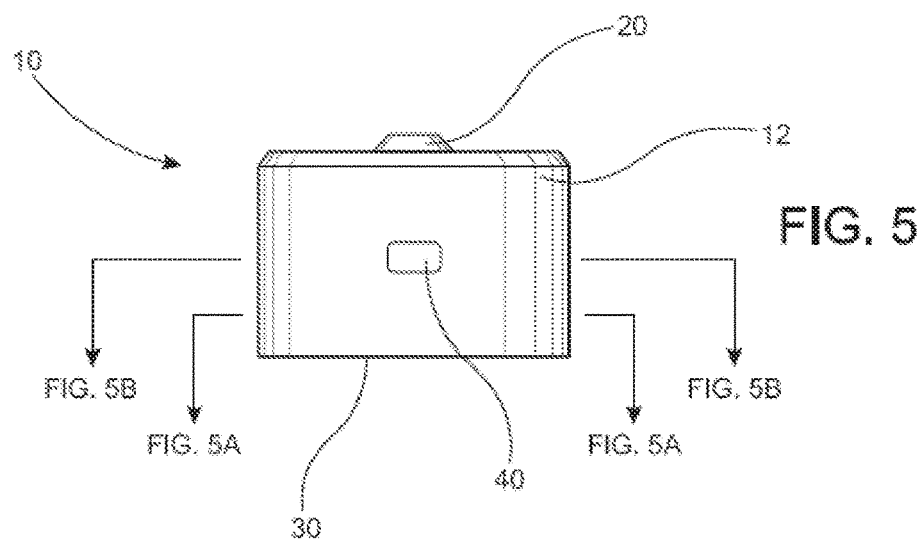
FIG. 5 is an exterior view of the closure assembly illustrated in FIG. 1 in a fully assembled orientation, and with the component of FIGS. 3, 3A and 3B being visible through the window of the first component illustrated in FIG. 2A, labeled herein as "State 1."
Figure 5A:
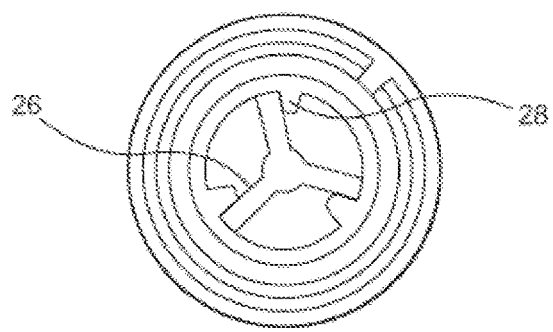
FIG. 5A is a sectional view of the interior of the closure assembly illustrated in FIG. 5, taken along lines B1-B1 of FIG. 5.
Figure 5B:
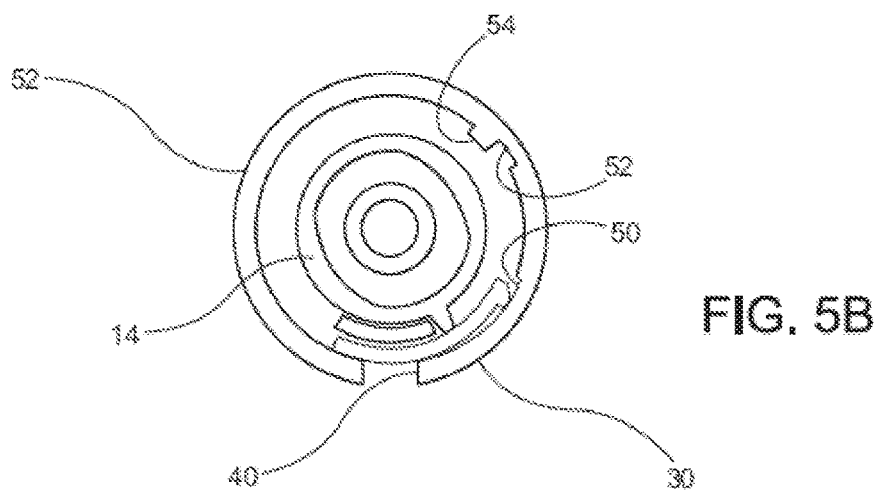
FIG. 5B is also a sectional view of the interior of the closure assembly illustrated in FIG. 5, but taken along lines C1-C1 of FIG. 5.
Figure 6:
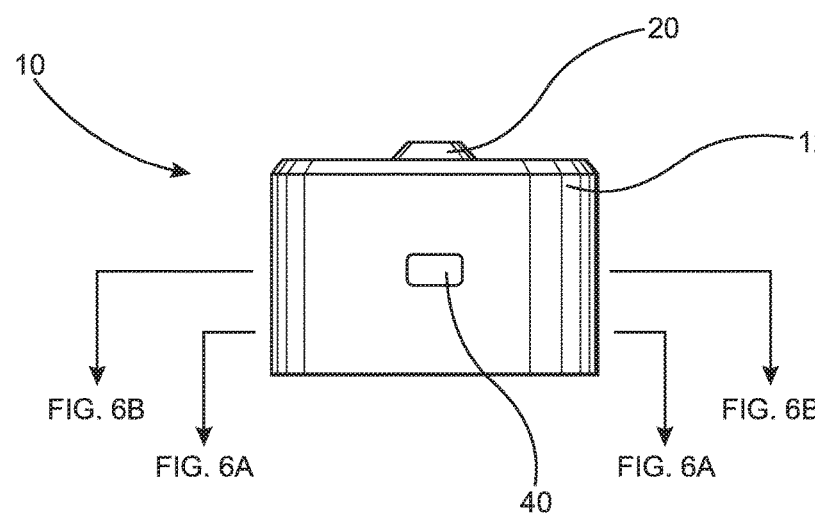
FIG. 6 is also an exterior view of the closure assembly illustrated in FIG. 1 in a fully assembled orientation, but with the component of FIGS. 4 and 4A, being visible through the window of the first component illustrated in FIG. 2A, and labeled herein as "State 2."
Figure 6A:
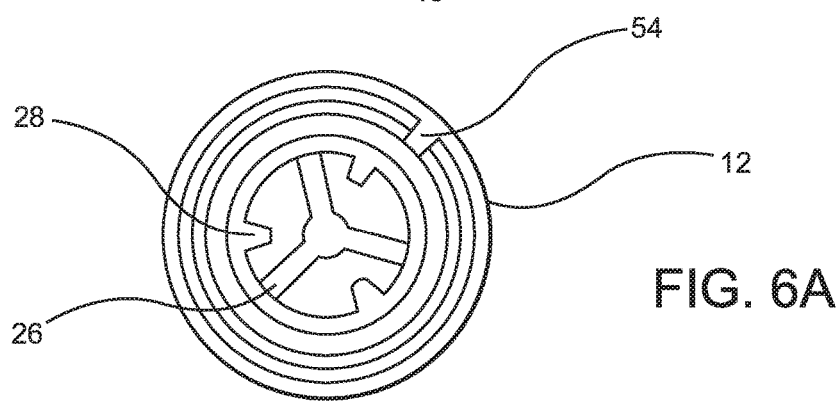
FIG. 6A is a sectional view of the interior of the closure assembly illustrated in FIG. 6, taken along lines B2-B2 of FIG. 6.
Figure 6B:
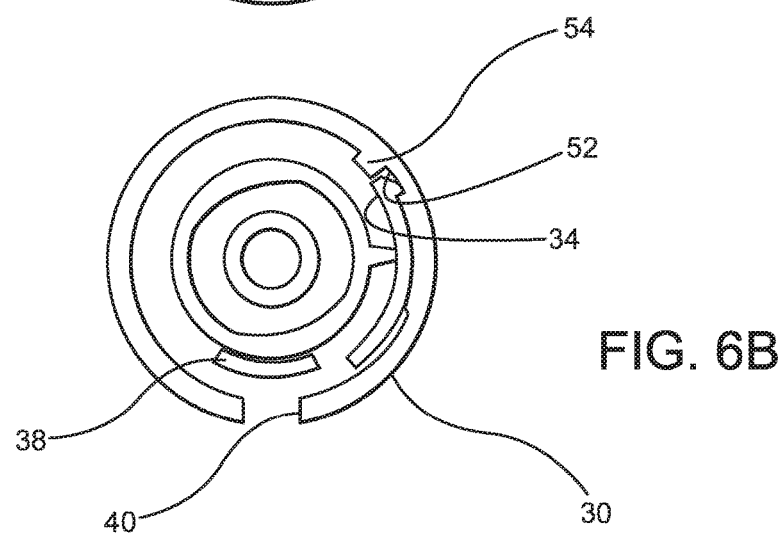
FIG. 6B is also a sectional view of the interior of the closure assembly illustrated in FIG. 6, but taken along lines C2-C2 of FIG. 6.

In describing the operation and use of the closure assembly 10, reference will be made herein to FIGS. 5-5B indicating the closure assembly 10 as being in a first retained position, indicated in the Figures as "State 1." Similarly, reference will also be made herein to "State 2" which is indicative of another operative orientation or state of use of the closure assembly as shown in FIGS. 6 to 6B. Moreover, "State 3" and "State 4" represent further orientations/positions and/or state of use of the closure assembly 10 as whether or not the closure assembly 10 has been used and/or in a possibly tampered with condition or state.

With initial reference now to the closure assembly 10 being in "State 1," as represented in FIGS. 5-5B, the closure assembly 10 is represented as it would appear prior to installation on a medical fitting. The closure assembly 10 would also appear in this same state after installation, but before any attempted removal of the closure assembly 10 from the enteral fitting or other medical device to which it is attached. As represented in FIG. 5, the indicator member 30 associated with the tip cap 16 is, in a preferred embodiment, green in color, and is readily viewable through the window 40 of the sleeve 12 when in "State 1." This indicates that the closure assembly 10 either has not been used or has been attached to or installed on a cooperating enteral component/fitting, but not removed therefrom. Further, and as represented in FIG. 5A the rotational position of the tip cap 16 is constrained in the clockwise ("CW") direction by the primary drive mechanism 24. That is to say, by the operative disposition of the spider hub 26 on the end cap 14 and the drive members 28 on the tip cap 16.

Further, the rotational position of the tip cap 16 is constrained in the counterclockwise ("CCW") direction by protrusion 34 on the indicator member 30 being disposed in a first snap position 50 formed on the interior surface of the sleeve 12, as represented in FIG. 5B. In order to pass or force the indicator member 30 beyond the first snap position 50, the protrusion 34 and snap feature of the indicator member 30 must deflect out of the first snap position 50. However, such deflection of the protrusion 34 and snap feature requires that a deliberate rotational force be applied to the sleeve 12 by a user. Returning to a description of this "State 1" though, it represents the closure assembly 10 being in an unused state, in terms of not having been attached to a medical device, and in an un-tampered with state, if still connected to the Enteral or other medical device, as intended.

With reference now to FIG. 6, the closure assembly in "State 2" shows the closure assembly 10 as it would appear after a person has begun to apply a counterclockwise rotation, in a "removal direction," wherein the "red" shield will be viewed through window 40. However, before the indicator member 30 has been broken, such as by being detached from the exterior of the tip cap 16 through a fracturing of the frangible member 32 or before it is disposed in a second snap position 52, it may be returned to the "State 1" position. Accordingly, when the indicator member 30 is in either the "State 1" or "State 2" position or orientation the indicator member 30 may be viewed through the window 40, by virtue of the ability to move the indicator member back from the "State 2" position to the "State 1" position. Therefore, the closure assembly 10 may be returned to its original and/or initial position of "State 1", wherein the window 40 will be green or visually expose the indicator member 30.

In the alternative, the closure assembly 10 may be moved ahead to a "State 3", as explained with primary reference to FIGS. 7-7B. However, in "State 3" the rotational position of the tip cap 16 is constrained in both directions (CW and CCW) by the protrusion 34 and snap feature being disposed in the second snap position, indicated in FIGS. 5B and 6B as 52. It is further of note that if any further or significant counterclockwise rotational force is applied to the closure assembly 10, the protrusion 34 and snap feature will engage the hard scap structure shown as at 54 in FIGS. 5B and 6B, it will cause the frangible tab 32 connecting the indicator member 30 to the exterior of the tip cap 16 to break and dispose the indicator member 30 in a detached position, as represented in at least in FIGS. 6-6A, 7-7A and 8-8A.

As a result, and with reference now to FIGS. 7, 7A and 7B, when the indicator member 30 of the tip cap 16 is in a "State 3" position, it will become disconnected from the tip cap 16, thereby permanently leaving the indicator member 30 in a disconnected position relative to the tip cap 16, as represented in FIG. 7B. Further, a disconnection of the indicator member 30 will allow the tip cap 16 to move freely with the sleeve 12 in either direction within the interior of the sleeve 12, due to the driving interaction between drive members 26 and 28. It is further noted that the force required to break the frangible member 32 must be less than the force required to unscrew the closure assembly 10 from the enteral component or other device to which it is attached. At this point, the shield 38 of the end cap 14 will be visible through the window 40 of sleeve 12, causing the window 40 to appear "red" in color, indicative of the color of the shield 38, and further indicative of the fact that the closure assembly 10 has been used and or tampered with and/or removed from the cooperating enteral fitting component.

"State 3" and "State 4" represent the closure assembly 10 in a state after the indicator member 30 has been detached from the exterior of the tip cap 16. As such, the window 40 of the sleeve 12 provides an irreversible visual indication of the "red" shield 38 associated with end cap 14, upon disconnection of the indicator member 30 from the tip cap 16. In either of these "States 3 or 4" the tip cap 16 can freely rotate, allowing for both installation and removal of the closure assembly 10 from the enteral or other device to which it is attached. This feature allows the user to reattach the closure assembly 10 to an enteral fitting component after it has been used, if that should be desired, while maintaining evidence or indication of use and/or tampering, because the window 40 in the sleeve 12 will always provide a viewing of the "red" shield 38. Accordingly, it is to be emphasized that the closure assembly 10 can be considered a "single use" device in that after disconnection of the indicator member 30, the shield 38 of end cap 14 will be irreversibly viewable through the window 40. This indicates that the closure assembly 10 has been removed from the intended enteral device and/or has been tampered with. Therefore, even though the closure assembly 10 may be repeatedly attached to and removed from a cooperative enteral fitting/component, it may still be considered a "single use" device in that the "red" indicator shield 38 will always be viewable through the window 40.

Figure 8:
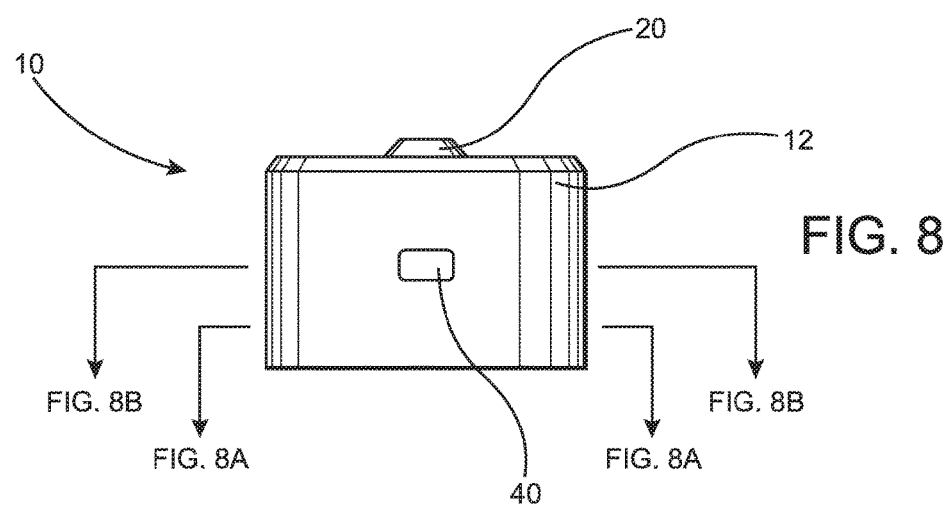
FIG. 8 is also an exterior view of the closure assembly illustrated in FIG. 1 in an assembled orientation, and labeled as "State 4."
Figure 8A:
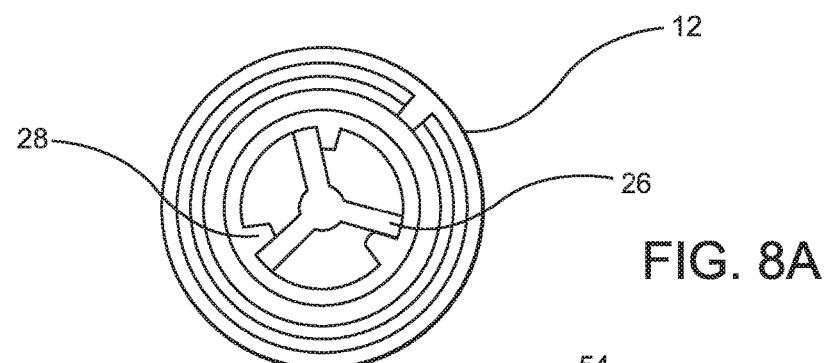
FIG. 8A is a sectional view of the interior of the closure assembly illustrated in FIG. 8, taken along lines B2-B2 of FIG. 8.
Figure 8B:
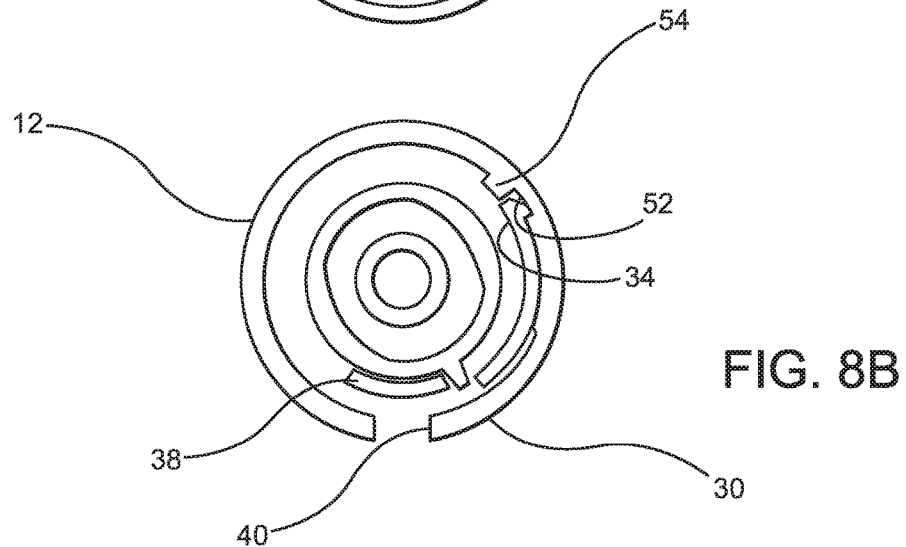
FIG. 8B is also a sectional view of the interior of the closure assembly illustrated in FIG. 8, but taken along lines C2-C2 of FIG. 8.

As further represented in FIGS. 7B and 8B, the indicator member 30 when disconnected from the tip cap, remains fixed within the sleeve 12 due to engagement of the protrusion 34 and snap feature with the second snap position, 52. As a result, and as set forth above the window 40 will always appear "red" through an irreversible viewing of the shield 38, once the indicator member 30 is detached from the tip cap 16.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly for a medical device structured to provide an indication of tampering, said closure assembly comprising:
   an outer sleeve including an indicator window,
   an end cap connected to said sleeve and movable there with, said end cap including an indicator shield,
   a tip cap movably retained within said sleeve and including an indicator member removably connected to said tip cap,
   said indicator member movable with said tip cap, within said outer sleeve, between at least a first retained position and a detached position,
   said first retained position comprising said indicator member disposed in visually observable relation with said indicator window,
   said first retained position further comprising said indicator member positioned in a visually obscuring relation to said indicator shield, relative to said indicator window,
   said detached position comprising said indicator member removed from said tip cap, and
   said detached position further comprising said indicator shield disposed in a viewable position within said outer sleeve, relative to said indicator window.

2. The closure assembly as recited in claim 1 wherein said indicator member is movable with said tip cap, within said outer sleeve, into a second retained position, said second retained position comprising said indicator member movable with said tip cap into and out of a visually obscuring disposition of said indicator shield relative to said indicator window.

3. The closure assembly as recited in claim 2 wherein said indicator member and said indicator shield each include a distinguishable visual coding independently viewable through said window.

4. The closure assembly as recited in claim 3 wherein said visual coding comprises a color coding.

5. The closure assembly as recited in claim 2 wherein said second retained position further comprises said indicator member connected to said tip cap and movable there with into and out of said visually observable relation with said indicator window.

6. The closure assembly as recited in claim 1 wherein said detached position further comprises said indicator member captured within said outer sleeve.

\* \* \* \* \*